United States Patent
Yamakawa et al.

(10) Patent No.: US 6,933,327 B2
(45) Date of Patent: Aug. 23, 2005

(54) DENTAL CURABLE COMPOSITION

(75) Inventors: Junichiro Yamakawa, Yamaguchi-ken (JP); Hideki Kazama, Yamaguchi-ken (JP)

(73) Assignee: Tokuyama Corporation, Yamaguchi (JP)

( * ) Notice: Subject to any disclaimer, the term of this patent is extended or adjusted under 35 U.S.C. 154(b) by 374 days.

(21) Appl. No.: 10/111,187

(22) PCT Filed: Aug. 16, 2001

(86) PCT No.: PCT/JP01/07062
§ 371 (c)(1),
(2), (4) Date: Apr. 22, 2002

(87) PCT Pub. No.: WO02/15847
PCT Pub. Date: Feb. 28, 2002

(65) Prior Publication Data
US 2003/0036582 A1 Feb. 20, 2003

(30) Foreign Application Priority Data

Aug. 22, 2000 (JP) .................. 2000-250825
Dec. 25, 2000 (JP) .................. 2000-392597
Feb. 27, 2001 (JP) .................. 2001-52857

(51) Int. Cl.$^7$ .................. A61K 6/083; C08K 9/06; C08K 3/34
(52) U.S. Cl. .................. 523/115; 523/116; 523/118; 523/213; 524/492
(58) Field of Search .................. 523/115, 116, 523/118, 213; 524/492

(56) References Cited

U.S. PATENT DOCUMENTS 5,773,489 A * 6/1998 Sato .................. 523/115

FOREIGN PATENT DOCUMENTS

| JP | A 107187 | 8/1979 |
| JP | A 09255516 | 9/1997 |

* cited by examiner

Primary Examiner—Tae H. Yoon
(74) Attorney, Agent, or Firm—Sherman & Shalloway

(57) ABSTRACT

A dental polymerizable and curable composition that can be used as a dental composite restorative featuring excellent handling property at the time of filling, a small contraction upon polymerization, a high bending strength, excellent surface smoothness and wear resistance, and a very good matching of color tone to the natural tooth after restored.

14 Claims, No Drawings

DENTAL CURABLE COMPOSITION

TECHNICAL FIELD

The present invention relates to a dental curable composition which can be preferably used as a dental restorative. More specifically, the invention is related to a dental curable composition which can be excellently handled, shrinkage little upon the polymerization, and, when cured, exhibits excellent strength, surface smoothness, wear resistance and color tone that matches with that of natural teeth.

BACKGROUND ART

A dental composite restorative is finding a widespread use as a material for restoring the treated teeth since it is capable of imparting a color tone close to that of natural teeth and is easy to handle. In recent years, the dental composite restorative has been used not only for chiefly treating the anterior teeth but also for restoring the posterior teeth which must bear high occlusal pressures.

Generally, the dental composite restorative is chiefly constituted by a polymerizable monomer, a filler and a polymerization catalyst. The handling property of the paste thereof before being cured, and aesthetic appearance and mechanical properties of the cured product thereof, however, are greatly dependent upon the kind, shape, particle diameter and amount of filling of the filler that is used.

For example, there has heretofore been known a dental composite restorative blended with an inorganic filler having particle diameters of as relatively as several microns or more. This dental composite restorative has a feature in that a cured product thereof exhibits a large mechanical strength accompanied, however, by such problems that the polishing property and wear resistance are poor and that it is not capable of clinically offering a finished surface maintaining luster comparable to that of natural teeth.

In order to solve these problems, there has been proposed the use of inorganic particles having an average particle diameter of not larger than 1 μm and, particularly, the used of inorganic particles having a round shape and/or an inorganic filler of aggregates thereof, contributing to greatly improving the surface luster. With the dental composite restorative using such a fine filler, however, the fine filler has such a very large specific surface area that the paste thereof before being cured exhibits a large viscosity. In order to adjust the viscosity of the paste to such a level that a dentist can use it in the oral cavity, the polymerizable monomer must be blended in inevitably an increased amount causing a decrease in the handling property, an increase in the amount of contraction upon polymerization and a decrease in the mechanical strength.

In order to solve these problems, there has been proposed a method of using an organic/inorganic composite filler as disclosed in, for example, Japanese Unexamined Patent Publication (Kokai) No. 107187/1979. The organic/inorganic composite filler is obtained by mixing a fine inorganic powder and a polymerizable monomer together, polymerizing and curing them, followed by pulverization into particles of diameters of from about several tens to about several hundreds of microns. Use of this organic/inorganic composite filler makes it possible to solve the above-mentioned problem of handling property and Contraction due to the polymerization to some extent while realizing excellent surface smoothness and wear resistance which are the features obtained from the use of the fine filler.

With the dental composite restorative using the above-mentioned organic/inorganic composite filler, however, the color tone after restored is not necessarily in match with the color tone of the natural teeth and, hence, the aesthetic appearance is not satisfactory.

That is, even if there was selected a conventional material that met the color tone or transparency of a patient's teeth, it was not possible to correctly express the color tone or the quality appeal of the teeth, or the boundary between the filled product and the natural tooth became so distinct that a strong unnatural feeling could not be wiped off.

It has generally been said that light diffusion is one of the factors seriously affecting the aesthetic appearance among the optical properties possessed by the dental composite restorative. The light diffusion is a property in that light falling on a semitransparent material like the dental composite restorative, is refracted and reflected by the material filled in the restorative and is diffused into various directions. The reflected and diffused light that is observed acquires a color tone of the semi-transparent material and of a color tone reflecting the background color. It is therefore considered that the higher the light diffusion is, the more the contour is blurred between the natural tooth and the restored material or the background color of the restored material, enabling the color tone to become in match with the natural teeth.

As one of the indexes of light diffusion, there has been proposed a diffusion degree (D) that will be described later. Though it can be said that the light diffusion increases with an increase in the diffusion degree, Japanese Unexamined Patent Publication (Kokai) No. 255516/1997 proposes an art in which the diffusion degree of a dental composite material containing an inorganic filler is adjusted to lie within a predetermined range to adjust the light transmission of the material, thereby to improve aesthetic appearance. However, the above publication teaches that the above object is not accomplished unless there are used two kinds of inorganic fillers, i.e., an inorganic filler having an average particle diameter of not smaller than 1 μm and having a refractive index which is larger, by more than 0.06, than the refractive index of the polymerizable polymer that is cured, and an inorganic filler having an average particle diameter of not larger than 1 μm and having a refractive index which is larger, by not more than 0.06, than the refractive index of the polymerizable polymer that is cured. The above publication, however, does not even describe or suggest the improvement in the aesthetic appearance by adjusting the diffusion degree in a system using the organic/inorganic composite filler. The dental composite restorative containing the organic/inorganic composite filler exhibits optical properties which are different from that of a system that uses the inorganic filler. Therefore, the description of the above publication is not at all helpful in trying to bring the color tone into match with the natural tooth by using the system which contains the organic/inorganic composite filler.

Besides, the dental composite restorative using the above organic/inorganic composite filler is not still satisfactory concerning the handling property and mechanical strength, and further improvement is desired.

DISCLOSURE OF THE INVENTION

It is therefore an object of the present invention to provide a dental polymerizable and curable composition that can be used as a dental composite restorative featuring excellent handling property at the time of filling, a small contraction upon polymerization, a high bending strength, excellent surface smoothness and wear resistance, and a very good matching of color tone to the natural tooth after restored.

In order to solve the above-mentioned problems, the present inventors have conducted extensive study by using curable compositions containing the organic/inorganic composite filler concerning how the diffusion degree is affected by the components. As a result, the inventors have discovered the fact that the diffusion degree is seriously affected by the particle diameter of the organic/inorganic composite filler and by a difference in the refractive index between the organic/inorganic composite filler and a portion that becomes a matrix of the filler after cured, and that the diffusion degree of the cured product can be adjusted by controlling them. Based on this discovery, the inventors have further conducted the study to discover that the above-mentioned object can be achieved when the average particle diameter of the organic/inorganic composite filler is confined within a particular range and when the difference in the refractive index is increased to be not smaller than a particular value.

That is, the present invention is concerned with a dental curable composition containing an organic/inorganic composite filler having an average particle diameter of from 1 to 20 μm and a polymerizable monomer, wherein a cured product of said dental curable composition has a diffusion degree D as defined by the following formula, $$D=\{(I_{20}/\cos 20°)+(I_{70}/\cos 70°)\}/(2\times I_0)$$

wherein $I_0$, $I_{20}$ and $I_{70}$ denote intensities of light that has passed through in the directions of 0°, 20° and 70° with respect to the direction of incidence of light when light is permitted to fall perpendicularly onto the surface of a plate-like sample having a thickness of 0.3 mm obtained by curing said dental curable composition,
of not smaller than 0.01.

The dental curable composition of the present invention can be produced by the following method of production of the present invention.

That is, in producing the dental curable composition by mixing a polymerizable monomer composition and an organic/inorganic composite filler having an average particle diameter of from 1 to 20 μm together, a refractive index of said organic/inorganic composite filler and a refractive index of the cured product obtained by curing said polymerizable monomer composition, are so adjusted that a difference therebetween is not smaller than 0.01 in an absolute value.

From the standpoint of constituent components, therefore, the dental curable composition of the present invention contains an organic/inorganic composite filler and a polymerizable monomer, the organic/inorganic composite filler satisfying the following conditions (1) and (2):
(1) an average particle diameter is from 1 to 20 μm; and
(2) when a refractive index thereof is denoted by $n_F$ and a refractive index of a matrix portion in which said organic/inorganic composite filler is dispersed in a cured product obtained by curing said dental curable composition, is denoted by $n_M$, then, an absolute value of $n_F - n_M$ is not smaller than 0.01.

According to the present invention, though not theoretically limited, it is considered that use of the organic/inorganic composite filler works to decrease the contraction due to the polymerization like the conventional dental curable composition, and to improve the surface smoothness and wear resistance of the cured product. Besides, since the composite filler has an average particle diameter which is larger than the wavelength (0.4 to 0.7 μm) of a visible light ray, the light is effectively refracted and reflected. Further, since a difference in the refractive index is great between the composite filler and the matrix, light falling into the cured product is refracted and reflected on the interface between the composite filler and the matrix compounded due to an increase in the diffusion degree, contributing to improving the matching of color tone with the color tone of the natural teeth.

The dental curable composition of the present invention exhibits particularly high surface smoothness and wear resistance when the organic/inorganic composite filler is the one obtained by pulverizing the cured product of the polymerizable and curable composition that contains a polymerizable monomer and spherical or nearly spherical inorganic particles having an average particle diameter of from 0.001 to 1 μm and/or aggregates of the inorganic particles.

In particular, the refractive index can be easily adjusted for obtaining a desired diffusion degree and an X-ray contrast can be easily imparted when the organic/inorganic composite filler contains an inorganic oxide obtained by reacting an organosilicon compound which is hydrolyzable and an organic compound of at least one kind of metal selected from the group consisting of metals of the Groups I, II, III and IV of periodic table which can be bonded to the organosilicon compound which is hydrolyzable, as inorganic particles and/or aggregates of inorganic particles which are chief constituent components.

When the dental curable composition of the present invention further contains an inorganic filler comprising spherical or nearly spherical inorganic particles having an average particle diameter of not larger than 1 μm and/or aggregates of the inorganic particles, the curable paste thereof can be favorably handled, and the cured product thereof exhibits a further increased strength.

In particular, contraction upon the polymerization decreases, the curable paste becomes less powdery and the filling operation becomes more easy, when the inorganic filler is treated for its surfaces with a silane compound represented by the following general formula,

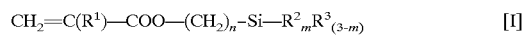

$$CH_2=C(R^1)-COO-(CH_2)_n-Si-R^2{}_mR^3{}_{(3-m)} \qquad [I]$$

wherein $R^1$ is a hydrogen atom or a methyl group, $R^2$ is an alkoxy group having 1 to 6 carbon atoms, an isocyanate group or a chlorine atom, $R^3$ is a hydrocarbon group having 1 to 6 carbon atoms, m is 2 or 3, and n is an integer of 8 to 20.

When the organic/inorganic composite filler contains a fluorescent whitening agent, further, the cured product of the dental curable composition of the present invention becomes highly transparent making it possible to easily obtain a color tone close to colorlessness.

In particular, the above-mentioned effects are highly efficiently obtained when the cured product has a yellowness index (YI) as defined by the following formula, Yellow color degree $(YI)=100\times(1.28X-1.06Z)/Y$ wherein X, Y and Z are three stimulus values of when a sample having a thickness of 2 mm is measured by using a color-difference meter with the sample being closely adhered to a white background,
of not larger than 20.

BEST MODE FOR CARRYING OUT THE INVENTION

The dental curable composition of the present invention contains an organic/inorganic composite filler (hereinafter simply referred to as composite filler) and a polymerizable monomer. By using the organic/inorganic filler as a filler, it is made possible to decrease the contraction due to the polymerization and to improve the surface smoothness and the wear resistance of the cured product. Here, the composite filler stands for the one comprising a polymer and inorganic particles, and can be obtained by, for example, pulverizing a cured product obtained by curing a polymerizable and curable composition containing a polymerizable monomer and an inorganic powder.

There is no particular limitation on the composite filler used for the dental curable composition of the present invention so far as its average particle diameter is from 1 to 20 μm. In order to accomplish the object of the present invention, however, it is desired that when the composite filler has a refractive index $n_F$ and a matrix portion in which the composite filler is dispersed in the cured product that is obtained by curing the dental curable composition of the invention, has a refractive index $n_M$, then, an absolute value of $n_F - n_M$ is not smaller than 0.01. A method of producing the composite filler will be described later concerning a preferred method of producing a dental curable composition of the present invention.

Though there is no particular limitation on the content of the composite filler in the dental curable composition of the present invention, it is desired that the content of the composite filler is from 30 to 90% by mass and, particularly, from 40 to 70% by weight based on the mass of the whole dental curable composition from the standpoint of matching of color tone between the cured product and the natural teeth and the strength.

As the polymerizable monomer used for the dental curable composition of the present invention, there can be used any known polymerizable monomer that has been used as a dental composite material without any limitation. Examples of the polymerizable monomer that can be preferably used may be polymerizable monomers having a (meth)acryloyl group. Concretely, there can be exemplified the following polymerizable monomers A to D.

A. Monofunctional Vinyl Monomers:

Methacrylates such as methyl methacrylate, ethyl methacrylate, isopropyl methacrylate, hydroxyethyl methacrylate, tetrahydrofurfuryl methacrylate, glycidyl methacrylate, and acrylates corresponding to these methacrylates; and acrylic acid, methacrylic acid, p-methacryloyloxybenzoic acid, N-2-hydroxy-3-methacryloyloxypropyl-N-phenylglycin, 4-methacryloyloxyethyltrimellitic acid, and anhydrides thereof, 6-methacryloyloxyhexamethylenemalonic acid, 10-methacryloyloxydecamethylenemalonic acid, 2-methacryloyloxyethyldihydrogen phosphate, 10-methacryloyloxydecamethylenedihydrogen phosphate, and 2-hydroxyethylhydrogenephenyl phosphonate.

B. Bifunctional Vinyl Monomers:

B-1. Those of the Aromatic Compounds:

2,2-Bis(methacryloyloxyphenyl)propane, 2,2-bis[4-(3-methacryloyloxy)-2-hydroxypropoxyphenyl]propane (hereinafter abbreviated as bis-GMA), 2,2-bis(4-methacryloyloxyphenyl)propane, 2,2-bis(4-methacryloyloxypolyethoxyphenyl)propane (hereinafter abbreviated as D-2.6E), 2,2-bis(4-methacryloyloxydiethoxyphenyl)propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2-(4-methacryloyloxyethoxyphenyl)-2-(4-methacryloyloxydiethoxyphenyl)propane, 2-(4-methacryloyloxydiethoxyphenyl)-2-(4-methacryloyloxyditriethoxyphenyl)propane, 2-(4-methacryloyloxydipropoxyphenyl)-2-(4-methacryloyloxytriethoxyphenyl)propane, 2,2-bis(4-methacryloyloxypropoxyphenyl)propane, 2,2-bis(4-methacryloyloxyisopropoxyphenyl)propane, and acrylates corresponding to these methacrylates; and diadduct obtained by the addition reaction of a vinyl monomer having an —OH group like such methacrylate as 2-hydroxyethyl methacrylate, 2-hydroxypropyl methacrylate or 3-chloro-2-hydroxypropyl methacrylate, or an acrylate corresponding to these methacrylates and a diisocyanate compound having an aromatic group, such as diisocyanatemethyl benzene or 4,4'-diphenylmethane diisocyanate.

B-2. Those of the Aliphatic Compounds:

Ethylene glycol dimethacrylate, diethylene glycol dimethacylate, triethylene glycol dimethacrylate (hereinafter abbreviated as 3G), butylene glycol dimethacrylate, neopentyl glycol dimethacrylate, propylene glycol dimethacrylate, 1,3-butanediol dimethacrylate, 1,4-butanediol dimethacrylate, 1,6-hexanediol dimethacrylate, and acrylates corresponding to these methacrylates;

diadducts obtained by the addition reaction of a vinyl monomer having an —OH group like such methacrylate as 2-hydroxyethyl methacrylate, 2-hydroxypropyl methacrylate, 3-chloro-2-hydroxypropyl methacrylate or acrylate corresponding to the methacrylate and a diisocyanate compound such as hexamethylene diisocyanate, trimethylhexamethylene diisocynate, diisocynatemethylcyclohexane, isophorone diisocyanate, or methylenebis(4-cyclohexyl isocyanate); and acrylic anhydride, methacrylic anhydride, 1,2-bis(3-methacryloyloxy-2-hydroxypropoxy)ethyl, and di(2-methacryloyloxypropyl)phosphate.

C. Trifunctional Vinyl Monomers:

Methacrylates such as trimethylolpropane trimethacrylate, trimethylolethane trimethacrylate, pentaerythritol trimethacrylate and trimethylolmethane trimethacrylate, and acrylates corresponding to these methacrylates.

D. Tetrafunctional Vinyl Monomers:

Pentaerythritol tetramethacrylate and pentaerythritol tetraacrylate; and adducts obtained by the addition reaction of a diisocyanate compound such as diisocyanatemethylbenzene, diisocyanatemethylcyclohexane, isophoronediisocyanate, hexamethylenediisocyanate, trimethylhexamethylenediisocyanate, methylenebis(4-cyclohexylisocyanate), 4,4-diphenylmethanediisocyanate or tolylene-2,4-diisocyanate with a glycidol dimethacrylate.

These polymerizable monomers can be used in a single kind or being mixed together in two or more different kinds.

Though there is no particular limitation on the content of the polymerizable monomer used in the dental curable composition of the present invention, it is desired that the content of the polymerizable monomer is from 15 to 99% by mass and, particularly, from 20 to 60% by weight based on the mass remaining after the mass of the composite filler is removed from the mass of the whole dental curable composition from the standpoint of filling the curable paste and the strength of the cured product.

In order to further increase the strength of the cured product and to adjust the refractive index, it is desired to blend the dental curable composition of the present invention with an inorganic filler (hereinafter also referred to as a fine filler of the third component) which comprises inorganic particles having an average particle diameter of not larger than 1 μm and/or aggregates of the inorganic particles while improving the handling property for filling the paste by increasing the viscosity and suppressing the paste from becoming powdery that inevitably results from the use of the composite filler.

Though there is no particular limitation on the shape of the fine filler of the third component, it is desired to use spherical or nearly spherical inorganic particles and/or aggregates thereof in order to obtain a high surface smoothness and a high wear resistance. The word "nearly spherical" used here stands for that the particles are round-shaped as observed within a unit visible field by taking a picture of the filler using a scanning electron microscope (hereinafter referred to as SEM), having an average degree of symmetry obtained by dividing the particle diameter in a direction at right angles with the maximum diameter thereof by the maximum diameter thereof of not smaller than 0.6.

In order to obtain a high surface smoothness, a high wear resistance and a high mechanical strength, further, it is desired that the fine filler of the third component has an average particle diameter of from 0.001 to 0.7 $\mu$m and, particularly, from 0.05 to 0.7 $\mu$m. It is further desired that the fine filler of the third component as a whole counting an aggregate as a particle, has an average particle diameter of from 0.001 to 100 $\mu$m and, particularly, from 0.05 to 50 $\mu$m. Even when the inorganic filler contains aggregates having a large particle diameter, the smoothness and wear resistance are not degraded after the polymerization and curing unlike the case of when independent particles having large particle diameters are added, provided the aggregates comprise inorganic particles having an average particle diameter of not larger than 1 $\mu$m.

In the fine filler of the third component, it is desired that the inorganic particles (primary particles) have such an excellent single dispersion property that a coefficient of variation in the particle diameter is not larger than 0.3 from the standpoint of surface smoothness and wear resistance of the cured product after the restoration. It is further desired to fire the inorganic particles at a temperature of from 500 to 1000° C. to decrease the silanol groups on the surface and to maintain surface stability of the inorganic filler itself. It is allowable to use a plurality of kinds of inorganic fillers having different particle size distributions and of different materials being mixed together.

There is no particular limitation on the material of the fine filler of the third component, and there can be used such inorganic compounds as inorganic oxides like amorphous silica, silica-zirconia, silica-titania, silica-titania-barium oxide, quartz and alumina. As the inorganic filler, there is particularly preferably used a composite oxide comprising chiefly silica and zirconia, since it imparts X-ray contrast property and yields a cured product having excellent wear resistance.

Though there is no particular limitation on the method of producing the inorganic powder, it is desired to produce the inorganic powder by a so-called sol-gel method which is advantageous for industrially producing the fine particles having a spherical or a nearly spherical shape and a distribution of single dispersion, and from the standpoint of easily adjusting the refractive index and easily imparting the X-ray contrast property. On account of the foregoing reasons, there can be particularly desirably employed a method in which a mixture solution of an organosilicon compound that can be hydrolyzed and an organic compound of at least one metal selected from the group consisting of metals of the Groups I, II, III and IV of periodic table capable of being bonded to the organosilicon compound that is hydrolyzable, is added to an alkaline solvent which dissolves these organic compounds but does not substantially dissolve the reaction product, and the hydrolysis is then conducted to precipitate the reaction product which is then dried.

The inorganic oxide obtained by this method may be fired at a temperature of 500 to 1000° C. after drying to maintain surface stability. Since the inorganic oxide may be partly aggregated during the firing, it is desired to digest the aggregated particles by using a jet mill or a vibration ball mill to adjust the particle size. Despite of executing these operations, it is difficult to completely bring the aggregated particles back to the state of before being aggregated. When the above-mentioned heat treatment is conducted, therefore, there is obtained a filler of a mixture of the inorganic particles having an average particle diameter of not larger than 1 $\mu$m and aggregates thereof.

Though there is no particular limitation on the content of the fine filler of the third component, it is desired that the content of the fine filler of the third component is from 1 to 85% by mass and, particularly, from 40 to 80% by mass based on the mass remaining after the mass of the composite filler is removed from the mass of the whole dental curable composition from the standpoint mentioned in the foregoing.

As will be described later, it is desired that the fine filler of the third component is used after the surfaces thereof have been treated to be hydrophobic.

The dental curable composition of the present invention is cured by polymerizing the polymerizable monomer by using a polymerization initiator (polymerization catalyst). It is therefore desired that the dental curable composition of the present invention contains the polymerization initiator.

As the polymerization initiator, there can be used known polymerization initiators without any limitation. In general, the polymerization initiator of a different kind is used depending upon means for polymerizing the polymerizable monomer. The polymerization means may be the one that utilizes light energy such as ultraviolet rays or visible rays, the one that utilizes the reaction with a peroxide and a promoter, or the one that utilizes heating. A polymerization initiator may be suitably selected out of the following variety of polymerization initiators depending upon the polymerization means that is employed.

As the polymerization initiator used for the reaction based on the light energy (hereinafter referred to as photopolymerization), there can be exemplified benzoinalkyl ethers such as benzoinmethyl ether, benzoinethyl ether and benzoinisopropyl ether; benzyl ketals such as benzyldimethyl ketal and benzyldiethyl ketal; benzophenones such as benzophenone, 4,4'-dimethylbenzophenone 4-methacryloxybenzophenone; α-diketones such as diacetyl, 2,3-pentadionbenzyl, camphorquinone, 9,10-phenanthraquinone and 9,10-anthraquinone; thioxanthone compounds such as 2,4-diethoxythioxanthone, 2-chlorothioxanthone and methylthioxanthone; and bisacylphosphine oxides such as bis(2,6-dichlorobenzoyl) phenylphosphine oxide, bis(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide and bis(2,4,6-trimethylbenzoyl)-phenylphosphine oxide.

A reducing agent is often added to the photopolymerization initiator. An example thereof may be tertiary amines such as 2-(dimethylamino)ethyl methacrylate, ethyl 4-dimethylaminobenzoate and N-methyldiethanolamine; aldehydes such as lauryl aldehyde, dimethylaminobenzaldehyde and terephthalaldehyde; and sulfur-containing compounds such as 2-mercaptobenzoxazole, 1-decanethiol, thiosalicylic acid and thiobenzoic acid.

As the polymerization initiator that can be used for the thermal polymerization, there can be exemplified peroxides such as benzoyl peroxide, p-chlorobenzoyl peroxide, tert-butylperoxy-2-ethyl hexanoate, tert-butylperoxy dicarbonate and diisopropylperoxy dicarbonate; azo compounds such as azobisisobutylonitrile and the like; boron compounds such as tributylborane, partial oxide of tributylborane, sodium tetraphenylborate, sodium tetrakis(p-fluorophenyl)borate and triethanolamine salt of tetraphenylboric acid; barbituric acids such as 5-butylbarbituric acid and 1-benzyl-5-phenylbarbituric acid; and sulfinates such as sodium benzenesulfinate and sodium p-toluenesulfinate.

In the dental curable composition, in general, photopolymerization is in many cases used as curing (polymerization) means owing to its easiness in operation. In the dental curable composition of the present invention, too, it is desired to use a photo-polymerization initiator as the polymerization initiator. Among the above-mentioned photo-polymerization initiators, concrete examples that can be particularly preferably used include camphorquinone, bis(2,4,6-trimethylbenzoyl)phenylphosphine oxide and bis (2,6-dimethoxybenzoyl)-2,4,4-trimethylphenylphosphine oxide. These polymerization initiators can be used alone but may be used being mixed in two or more kinds. The amount of addition of the polymerization initiator may be selected depending upon the object. Usually, however, the polymerization initiator is used in an amount of from 0.01 to 30 parts by weight and, more preferably, from 0.1 to 5 parts by weight per 100 parts by weight of the polymerizable monomer.

The dental composition of the present invention can be blended with known additives in a range in which they do not greatly impair the effect of the invention. The additives may be a polymerization inhibitor, a pigment, an ultraviolet ray absorber and the like. In order to further improve the strength of the cured product, the dental polymerizable composition of the present invention may be further blended with an inorganic filler having an average particle diameter which is not smaller than 1 $\mu$m within a range in which the surface smoothness and wear resistance are not deteriorated.

In the dental curable composition of the present invention, the greatest feature resides in that the diffusion degree D of the cured product is not smaller than 0.01. Here, the diffusion degree D is an index of light diffusion of when the cured product is irradiated with light, and is defined by the following formula, $$D=\{(I_{20}/\cos 20°)+(I_{70}/\cos 70°)\}/(2\times I_0)$$

wherein $I_0$, $I_{20}$ and $I_{70}$ denote intensities of light that has passed through in the directions of 0°, 20° and 70° C. with respect to the direction of incidence of light when light is permitted to fall perpendicularly onto the surface of a plate-like sample having a thickness of 0.3 mm obtained by curing said dental curable composition.

The light intensity (luminous intensity) can be easily measured by using a goniophotometer photometer. The trigonometric function (cos) means a cosine in a direction in which the luminous intensity is measured, and the unit of angle is in degrees (°).

Upon setting the diffusion degree to be not smaller than 0.01, the teeth can be restored by using the dental curable composition of the present invention maintaining a color tone close to that of natural teeth, i.e., maintaining a highly aesthetic appearance. To obtain a color tone that is more adapted, it is desired that the diffusion degree is not smaller than 0.05 and, more preferably, not smaller than 0.08. When the diffusion degree is too high, it becomes difficult to maintain transparency as the dental restorative. It is therefore desired that the diffusion degree is not larger than 0.5 and, more preferably, not larger than 0.3.

There is no particular limitation on the method of producing the dental curable composition of the present invention. The dental curable composition of the invention, however, can be suitably produced by the following method (production method of the invention).

That is, in producing the dental curable composition by mixing the polymerizable monomer composition (also referred to as starting composition of matrix) and the composite filler having an average particle size of from 1 to 20 $\mu$m, the mixing is so adjusted that an absolute value of a difference between the refractive index of the composite filler ($n_F$) and the refractive index of the cured product obtained by curing the monomer composition is not smaller than 0.01.

When there is used the composite filler having an average particle size which is smaller than 1 $\mu$m, it becomes difficult to obtain the dental curable composition that gives the diffusion degree of not smaller than 0.01. When there is used the composite filler having an average particle diameter which is larger than 20 $\mu$m, there arouses a problem in the handling property such as becoming powdery or sticky accompanied by a decrease in the mechanical strength, which is not desirable. From the standpoint of obtaining the dental restorative of which the cured product exhibits a large mechanical strength, the curable paste of which can be excellently handled, and which possesses a higher diffusion degree, it is desired to use a composite filler having an average particle diameter of from 2 to 18 $\mu$m and, more preferably, from 5 to 15 $\mu$m.

The composite filler used in the production method of the present invention may be the one produced by any known method provided its average particle diameter is from 1 to 20 $\mu$m and its refractive index satisfies the above-mentioned conditions. Hence, there is no particular limitation on the particle size distribution thereof or on the production method thereof. In order to obtain a high surface smoothness, a large wear resistance and a large mechanical strength, it is desired that the composite filler is the one obtained by pulverizing a cured product of the polymerizable and curable composition (also referred to as starting composition for the composite filler) that contains a polymerizable monomer (hereinafter also referred to as starting monomer for the composite filler) and an inorganic powder (also referred to as starting inorganic filler for the composite filler) comprising spherical or nearly spherical inorganic particles having an average particle diameter of from 0.001 to 1 $\mu$m and, particularly, from 0.05 to 0.7 $\mu$m and/or aggregates of the inorganic particles.

As the starting inorganic filler for the composite filler, there can be used the one same as that of the above-mentioned fine filler of the third component. That is, there is preferably used an inorganic filler having such an excellent monodispersion property that a coefficient of change of the primary particle diameters is not Larger than 0.3, having an average particle diameter of the inorganic powder as a whole of from 0.001 to 20 $\mu$m and, particularly, from 0.05 to 5 $\mu$m. The above inorganic particles make it possible to obtain a cured product thereof having an X-ray contrast and more excellent wear resistance. It is therefore, desired that the inorganic particles are those of a composite oxide containing silica and zirconia as chief constituent components.

The starting inorganic filler for the composite filler may be a mixture of a plurality of kinds of those having different particle size distributions and materials. Besides, the inorganic filler, too, may desirably be used by treating the surfaces thereof to be hydrophobic.

There is no particular limitation, either, on the starting monomer for the composite filler. The polymerizable monomers which are the same as those described above as the components of the curable composition of the present invention, can be used in one kind or in a combination of a plurality of kinds. There is no particular limitation on the ratio of the amounts of the starting inorganic filler for the composite filler and the starting monomer for the composite filler in the starting composition for the composite filler, and the ratio may be suitably determined from the standpoint of strength and refractive index of the obtained composite filler. Preferably, however, the starting inorganic filler for the composite filler is used in an amount of from 40 to 95% by mass and, particularly, from 60 to 90% by mass based on the total mass of the starting inorganic filler for the composite filler and the starting monomer for the composite filler. It is further desired that a difference between the refractive index of the starting inorganic filler for the composite filler and the refractive index of the starting monomer for the composite filler is not larger than 0.1 and, more preferably, not larger than 0.03, so that the transparency of the cured product of the dental curable composition is not greatly deteriorated.

The starting composition for the composite filler may be further blended with a polymerization inhibitor, an ultraviolet-ray absorber, a pigment and the like in addition to the starting inorganic filler for the composite filler and the starting monomer for the composite filler.

The starting composition for the composite filler is cured by polymerization by being added with a photopolymerization catalyst and/or a chemical polymerization catalyst, and the obtained cured product is pulverized and classified to obtain a composite filler having a desired average particle diameter. The pulverization method is conducted suitably by using a ball mill, a vibration mill or a jet mill, and the classification is conducted by using a sieve, an air classifier or a hydraulic elutriation classifier.

The composite filler thus obtained may be washed, decolored and treated for their surfaces before being mixed to the starting composition of matrix. The decolorization is usually conducted by dispersing an organic/inorganic composite filler in a suitable solvent, dissolving a peroxide therein with stirring and, depending upon the cases, heating the solvent. As the peroxide, there is preferably used a known peroxide. The surface treatment is conducted in the same manner as that of treating the surfaces of the inorganic filler that will be described later.

It is desired that the composite filler contains a fluorescent whitening agent because of the reasons described below. That is, the composite filler is often colored and becomes yellowish during the polymerization or during the pulverization. When the composite filler is used for the dental restorative, therefore, it becomes very difficult to reproduce the color tone particularly when it is used for the incisal of teeth which are colorless having a clear color tone or when it is used for the teeth that are bleached.

Addition of a white pigment such as titanium oxide makes, the appearance white causing, however, the transparency to be decreased to a striking degree. Therefore, the above-mentioned problem is not solved by the addition of the white pigment. There has further been known a method of decoloring the organic/inorganic composite filler by using a decoloring reagent such as peroxide. However, many of the decoloring reagents usually involve danger in the handling thereof, and require the provision of a cumbersome step of decoloring without exhibiting a sufficient degree of decoloring effect.

On the other hand, upon containing the fluorescent whitening agent in the composite filler as described above, the yellowish color can be suppressed, and the dental curable composition is easily prepared having a high degree of transparency and a color tone which is almost colorless. This is because a very higher whitening effect is exhibited than that of when the fluorescent whitening agent is added to the paste.

Here, the fluorescent whitening agent stands for an agent which absorbs ultraviolet rays and emits violet blue to bluish green fluorescence near the short-wave side of the visible region, and does not necessarily represent an agent that is generally called fluorescent pigment. When the composite filler is not blended with the fluorescent whitening agent, it becomes difficult to suppress the yellowish color to a sufficient degree.

An yellow color degree is usually used as a parameter for evaluating the yellowness of the dental composite restorative. Here, the yellow color degree stands for a value calculated in compliance with the following formula, $$\text{Yellow color degree } (YI)=100\times(1.28X-1.06Z)/Y$$

wherein X, Y and Z are three stimulus values, by using, as a sample, a cured product of a dental composite restorative having a thickness of 2 mm which is closely adhered to a white background, and by measuring the three stimulus values of an XYZ color display system by using a color difference meter.

In order to reproduce the color tone close to colorlessness like that of an end of a tooth or a bleached tooth, it is desired that the yellow color degree calculated by the above-mentioned method is not larger than 20, more preferably, from 0 to 15 and, most preferably, from 0 to 10.

As the fluorescent whitening agent, there can be used any known ones without particular limitation. For example, there can be used derivatives of pyrazoline, stilbene, triazine, thiazole, benzoxazole, xanthone, triazole, oxazole, thiophene and cumarin. Concretely speaking, there can be exemplified such compounds as 4,4'-bis((diphenyltriazinyl) stilbene, stilbenyl-naphthotriazole, 2,2'-(thiophenediil)-bis (tert-butyl-benzoxazole), 2-(stilbyl-4")-(naphtho-1',2',4,5)-1,2,3-triazole-2"-sulfonic acid phenyl ester, 7-(4'-chloro-6"-diethylamino-1',3',5'-triazine-4'-il)-amino-3-phenyl-cumarin, 2,5-bis(6,6'-bis(tert-butyl)-benzoxazole-2-il) thiophene, 2,5-thiophenediil(5-tert-butyl-1,3-benzoxazole), 4,4'-bis(benzoxazole-2-il)stilbene, dibenzoxazolylethylene and N-methyl-5-methoxynaphthalimide.

These fluorescent whitening agent may be used in one kind or being mixed in two or more kinds. The amount of addition of the fluorescent whitening agent may be selected depending upon the object. Usually, however, the fluorescent whitening agent is used in an amount of from 0.0001) to 5 parts by weight, more desirably, from 0.001 to 0.5 parts by weight and, most desirably, from 0.005 to 0.05 parts by weight per 100 parts by weight of the polymerizable monomer (hereinafter also referred to as starting monomer for the composite filler) that is used for the production of the composite filler. When the amount of addition of the fluorescent whitening agent exceeds 5 parts by weight, properties of the dental composite restorative may be deteriorated. When the amount of addition is smaller than 0.0001 part by weight, the effect of the invention is not often exhibited to a sufficient degree.

The starting composition of matrix used in the production method of the present invention is the one obtained by removing the composite filler from the dental curable composition of the present invention. The cured product of the above composition is the one that serves as a matrix portion in which the composite filler is dispersed in the cured product that is obtained by curing the dental curable composition of the present invention. Accordingly, the refractive index of the cured product of the starting composition of matrix is synonymous to the refractive index ($n_M$) of the matrix portion.

As the polymerizable monomer used in the starting composition of matrix, there can be used those described above as the polymerizable monomers used for the dental curable composition of the present invention. The starting composition of matrix may be the same as the starting monomer for the composite filler. Here, however, the diffusion degree D can be easily adjusted to assume the above-mentioned value and the effect of the present invention can be particularly favorably exhibited when there are used those of different kinds but adjusting the absolute value of difference between the refractive index of the cured product thereof and the refractive index of the cured product of the starting monomer for the composite filler to be from 0.005 to 0.05 and, more preferably, from 0.01 to 0.03.

It is further desired to add a fine filler of the above-mentioned third component to the starting composition of matrix. Here, it is desired that the fine filler of the third component is used after the surfaces thereof are treated to be hydrophobic from the standpoint of improving the dispersion property in the polymerizable monomer. If the fine filler of the third component is used after having been treated to be hydrophobic, the dispersion property in the polymerizable monomer is improved, the cured product exhibits improved surface smoothness and wear resistance, contraction due to polymerization becomes small during the curing, and there is obtained a dental composite restorative that can be favorably handled at the time when it is to be applied and that features excellent balance in the properties.

As the hydrophobic property-imparting agent, there can be used a general-purpose silane coupling agent comprising an organosilicon compound, such as γ-methacryloyloxypropyltrimethoxysilane or hexamethyldisilazane. As the one which excellently exhibits the above-mentioned effect, however, it is desired to use a silane compound (also simply referred to as silane compound [I]) represented by the following general formula,

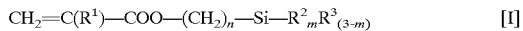

wherein $R^1$ is a hydrogen atom or a methyl group, $R^2$ is an alkoxy group having 1 to 6 carbon atoms, an isocyanate group or a chlorine atom, $R^3$ is a hydrocarbon group having 1 to 6 carbon atoms, m is 2 or 3, and n is an integer of 8 to 20.

When the above-mentioned general-purpose fine filler of the third component is used from the standpoint of surface smoothness and wear resistance of the cured product, in general, the viscosity increases too greatly. When added until powdery phenomenon disappears, the paste becomes sticky or the viscosity so increases that the paste cannot be easily spread, thus hindering the handling property. To prevent a decrease in the handling property by adjusting the viscosity, it becomes necessary to add a polymerizable monomer, resulting in an increase in the contraction due to polymerization. On the other hand, when there is used a fine filler of the third component of which the surfaces are treated with the hydrophobic property-imparting agent represented by the above-mentioned general formula, the paste does not become sticky and the handling property is not deteriorated despite the fine filler is added until powdery phenomenon disappears. It is thus allowed to obtain a dental composite restorative having a particularly favorable balance in the above-mentioned properties.

In the above-mentioned general formula [I], $R^1$ is a hydrogen atom or a methyl group, $R^2$ is an alkoxy group having 1 to 6 carbon atoms, an isocyanate group or a chlorine atom, $R^3$ is a hydrocarbon group having 1 to 6 carbon atoms, m is 2 or 3, and n is an integer of 8 to 20. When n lies in the above range, it is allowed to obtain a dental composite restorative in which the inorganic filler is dispersed particularly excellently in the polymerizable monomer, a paste thereof exhibits a viscosity that is increased very little, and is very excellent from the standpoint of handling property and contraction due to polymerization.

As the alkoxy group $R^2$ having 1 to 6 carbon atoms, there can be exemplified methoxy group, ethoxy group, n-propoxy group and iso-propoxy group. As the hydrocarbon group $R^3$ having 1 to 6 carbon atoms, there can be exemplified alkyl groups having 1 to 6 carbon atoms such as methyl group, ethyl group, n-propyl group and iso-propyl group as well as phenyl group.

Concrete examples of the silane compound that can be preferably used and is represented by the above general formula [I](hereinafter also referred to simply as silane compound [I]) include:

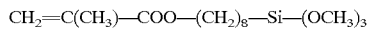

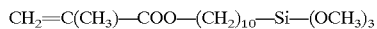

(hereinafter abbreviated as MDS)

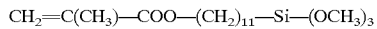

(hereinafter abbreviated as MUDS)

(hereinafter abbreviated as AOS)

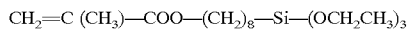

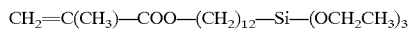

(hereinafter abbreviated as MDDTES)

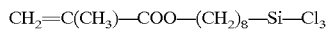

(hereinafter abbreviated as MOTCS)

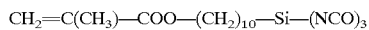

hereinafter abbreviated as MDTIS)

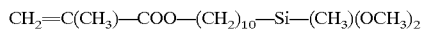

(hereinafter abbreviated as MDMMS)

The silane compounds [I] may be used in one kind but may be used being mixed in two or more kinds together. The silane compounds [I] may further be used in combination with a known surface treating agent other than the silane compounds [I].

There is no particular limitation on the treatment by using the above-mentioned hydrophobic property-imparting agent, and any known method can be used without limitation. Examples of the method of treatment for imparting hydrophobic property include a method of dispersing and mixing an inorganic filler and a hydrophobic property-imparting agent in a suitable solvent by using a ball mill or the like, drying them by using an evaporator or by spray-drying, and heating them at 50 to 150° C., a method of heating and refluxing the inorganic filler and the hydrophobic property-imparting agent in a solvent such as alcohol for several hours, a method that uses a titanate coupling agent, and a method of graft-polymerizing the surfaces of the particles with the polymerizable monomer.

The amount of the hydrophobic property-imparting agent used here is not particularly limited, but may be suitably determined upon experimentally confirming the mechanical properties of the composite restorative that is obtained. A suitable range of the amount is from 1 to 30 parts by weight of the hydrophobic property-imparting agent per 100 parts by weight of the inorganic filler.

The starting composition of matrix may be added with a polymerization inhibitor, a pigment, an ultraviolet-ray absorber and an inorganic filler having an average particle diameter of not smaller than 1 μm in a range in which they do not impair the effect of the present invention.

There is no particular limitation on the method of mixing components other than the polymerizable monomer in the starting composition for matrix. The components may be mixed into the polymerizable monomer prior to mixing the polymerizable monomer and the composite filler together, or the above two components may be mixed and, then, added to the mixture thereof.

In producing the dental curable composition that possesses a diffusion degree of not smaller than 0.01 by mixing the polymerizable monomer composition and a composite filler having an average particle diameter of 1 to 20 μm according to the production method of the present invention, it is important that an absolute value (hereinafter abbreviated as Δn) of a difference ($n_F-n_M$) between the refractive index ($n_F$) of the composite filler and the refractive index ($n_M$) of the cured product obtained by curing the polymerizable monomer composition, is not smaller than 0.01, preferably, from 0.01 to 0.04 and, more preferably, from 0.015 to 0.03.

Here, Δn is adjusted to be not smaller than 0.01 by changing the composition of the matrix monomer composition or of the starting composition for the composite filler, or both of them. In general, the refractive index ($n_M$) of the cured product of the matrix monomer composition can be increased by increasing the content of a polymerized monomer that is obtained by homopolymerizing the polymerizable monomer and has a high refractive index, or by adding a fine filler of the third component containing much component having a high refractive index (metal oxide such as of zirconium, barium or aluminum), the fine filler of the third component being added as required. Conversely, the refractive index ($n_M$) of the cured product of the matrix monomer composition can be lowered by increasing the content of a polymerized monomer that is obtained by homopolymerizing the polymerizable monomer and has a low refractive index, or by increasing the amount of addition of the fine filler of the third component having a low refractive index. The refractive index ($n_F$) of the composite filler can similarly be controlled by changing the starting monomer composition for the composite filler, by changing the ratio of the amount of the starting monomer for the composite filler and the amount of the starting inorganic filler for the composite filler, or by changing the composition of the starting inorganic filler for the composite filler.

In adjusting the absolute value Δn in the production method of the present invention, it is desired that the transparency (contrast ratio: C=Yb/Yw) of the cured product is brought into consideration, and the refractive indexes of the two are determined, so that the optical quality feeling of the cured product is brought closer to that of the natural teeth and that more aesthetic restoration can be accomplished. Here, the contrast ratio is represented by a ratio of Y-values (Yb and Yw) representing one of the three stimulus values of when a standard black plate (or a dark box) and a standard white plate are placed on the back side of the cured product of the dental restorative having a thickness of 1 mm, and also serves as an index of transparency. The contrast ratio is greatly affected by the refractive indexes of the components, by the amounts of blending and by the particle diameters, and cannot be exclusively specified. In general, however, it has been known that a composite resin becomes opaque as a difference in the refractive index increases between the cured product of the polymerizable monomer and the filler, and becomes transparent as the difference in the refractive index decreases. The dental restorative that is desirably used has a contrast ratio (C=Yb/Yw) of from 0.35 to 0.70 and, more preferably, from 0.5 to 0.65. In order to realize such a contrast ratio, it is desired that Δn is not smaller than 0.01 and, particularly, not smaller than 0.015 but is not larger than 0.1, preferably, not larger than 0.04 and, more preferably, not larger than 0.03.

In the production method of the present invention, it is desired that the difference in the transparency before the dental restorative is cured and after the dental restorative is cured is small. This is to facilitate the matching of color between the dental restorative that is filled in the dental clinic and the natural teeth, and to decrease a change in the transparency before and after the composition is cured by polymerization. A change in the transparency before and after the curing is greatly affected by the particle diameter of the filler and the amounts of blending the components, and cannot be exclusively specified. Generally, however, it is desired that an absolute value of a difference is decreased between Δn and the absolute value (Δn') of the difference between the refractive index of the starting composition for matrix before being cured and the refractive index ($n_F$) of the composite filler. The present invention which uses the composite filler makes it easy to adjust the refractive index as compared to the inorganic filler, and is particularly desirable.

The composite filler of which the difference Δn in the refractive index is adjusted and the matrix monomer composition are weighed in desired amounts, are kneaded together to a sufficient degree, and the paste thereof is defoamed under a reduced pressure to remove bubbles, thereby to obtain a dental curable composition of the present invention.

Though there is no particular limitation on the use, the dental curable composition of the present invention can be used as a composite resin for dental filling. A general method of use may be treating a cavity of a tooth to be restored with a suitable pretreating agent or an adhesive, filling the cavity directly with the composite resin for dental filling, forming the composite resin into the shape of a tooth, and irradiating the composite resin with intense light from a light irradiator.

The dental curable composition of the present invention highly diffuses light, enables the color tone to be very favorably adapted to the natural tooth, exhibits excellent handling property, little shrinkage upon the polymerization, has a high bending strength, and features excellent surface smoothness and wear resistance.

EXAMPLES

The invention will now be concretely described by way of examples to which only, however, the invention is in no way limited. The inorganic fillers, polymerizable monomers, polymerization initiators and fluorescent whitening agents used in Examples and in Comparative Examples were as described below.

[Inorganic Fillers]

F-1a: Spherical Silica-Zirconia

80 Grams of a tetraethyl silicate (product name: Ethyl Silicate 28, manufactured by Nihon Korucoat Kagaku Co.) was mixed into 400 g of an isobutyl alcohol (manufactured by Tonen Sekiyu Co.), and to which was added 5 g of an aqueous solution containing 0.05% of sulfuric acid, and the mixture was stirred at 40° C. for about one hour with stirring to conduct the hydrolysis. Then, to the above solution was mixed with stirring a solution obtained by dissolving 20 g of a tetrabutyl zirconate (manufactured by Nihon Soda Co.) and a sodium methylato methanol solution (concentration of 28% by weight) in 200 g of an isobutyl alcohol, thereby to prepare a mixed solution of tetraethyl silicate and tetrabutyl zirconate.

Next, 4 g of a tetraethyl silicate was added over a period of 30 minutes with stirring into an ammoniacal alcohol solution of 1000 g of methanol and 250 g of 25% ammonia water in a 3-liter glass container equipped with a stirrer and, then, the above mixed solution of tetraethyl silicate and tetrabutyl zirconate were added thereto dropwise over a period of about 6 hours. During the reaction, the temperature of the reaction vessel was maintained at 40° C. After the reaction, the solvent was distilled off the cloudy reaction vessel solution by using an evaporator, followed by drying at 80° C. under a reduced pressure to obtain a milky white powder. The milky white powder was fired at 950° C. for one hour, fed into an alumina pot of a diameter of 20 mm containing alumina balls, and was digested by using a ball mill for 5 hours. 100 Grams of the obtained inorganic particles were dispersed in 150 g of ethanol, and to which were added 3 g of a γ-methacryloyloxypropyltrimethoxysilane (MPS) and 1.5 g of water and were homogeneously mixed, and the mixture was distilled at 80° C. for 2 hours. The solvent was distilled off under a reduced pressure by using the evaporator, followed by drying at 80° C. under a reduced pressure to obtain an inorganic filler F-1a (Refractive Index of 1.520).

Observation of the silica-zirconia particles by using a scanning electron microscope revealed a mixture of independent spherical inorganic particles having an average particle diameter of 0.2 μm and aggregates of the spherical inorganic particles of 1 to 100 μm (average particle diameter of the whole particles being 20 μm).

F-1b: Spherical Silica-Zirconia

An inorganic filler was obtained in the same manner as F-1a but using the 10-methacryloyloxydecyltrimethoxysilane (MDS) instead of the MPS.

F-2a: Spherical Silica-Zirconia

Spherical silica-zirconia particles having a refractive index of 1.545 and an average particle diameter of 0.2 μm were obtained in the same manner as F-1a but changing the starting composition, and were treated for their surfaces with the MPS.

F-2b to 2h: Spherical Silica-Zirconia

Inorganic fillers F-2b to F-2h were obtained in the same manner as F-1 but using the surface-treating agents described below.

F-2b: MDS

F-2c:, 11-Methacryloyloxyundecyltrimethoxysilane (MUDS)

F-2d: 8-Acryloyloxyoctyltrimethoxysilane (AOS)

F-2e: 12-Methacryloyloxydodecyltriethoxysilane (MDDTES)

F-2f: 8-Methacryloyloxyoctyltrichlorosilane (MOTCS)

F-2g: 10-Methacryloyloxydecyltriisocyanatosilane (MDTIS)

F-2h: 10-Methacryloyloxydecylmonomethyldimethoxysilane (MDMMS)

F-3: Spherical Silica-Titania

Particles having a refractive index of 1.510, an average particle diameter of 0.2 μm and treated for their surfaces with the MPS.

F-4: Spherical Silica-Barium Oxide

Particles having a refractive index of 1.550, an average particle diameter of 0.2 μm and treated for their surfaces with the MPS.

F-5: Irregular Silica-Zirconia

Particles having a refractive index of 1.530, an average particle diameter of 3.0 μm and treated for their surfaces with the MPS.

[Polymerizable Monomers]

M-1: 2,2-Bis[(3-methacryloyloxy-2-hydroxypropyloxy) phenyl]propane (hereinafter abbreviated as bis-GMA)/ triethylene glycol dimethacrylate (hereinafter abbreviated as 3G)(weight ratio of 60/40); cured product has a refractive index of 1.546.

M-2: 1,6-Bis(methacrylethyloxycarbonylamino) trimethyloxane (hereinafter abbreviated as UDMA)/3G (weight ratio of 70/30); cured product has a refractive index of 1.510.

M-3: 2,2-Bis(4-methacryloyloxypolyethoxyphenyl)propane (hereinafter abbreviated as D-2.6E)/3G (weight ratio of 70/30); cured product has a refractive index of 1.550.

M-4: Bis-GMA/3G (weight ratio of 40/60); cured product has a refractive index of 1.534.

[Polymerization Initiators]

I-1: Azobisisobutylonitrile

I-2: Tert-butylperoxy-2-ethyl hexanoate

I-3: Benzoyl peroxide

I-4: Cumylperoxy octanoate

I-5: Bis(2,4,6-trimethylbenzoyl)phenylphosphine oxide

CQ: Camphorquinone

DMPT: N,N-Dimethyl-p-toluidine

[Fluorescent Whitening Agent]

W-1: 2,5-Thiophenediil(5-tert-butyl-1,3-benzoxazole)

W-2: 4,4'-Bis(benzoxazole-2-il)stilbene

W-3: N-Methyl-5-methoxy-naphtholimide

In the following Examples and Comparative Examples, the refractive indexes, diffusion degrees of the cured products, bending strengths of the cured products, surface smoothness of the cured products, handling property of the curable pastes, contraction due to polymerization and yellow degrees were measured and evaluated in accordance with the methods described below.

(1) Refractive Index.

The refractive indexes $n_D^{25}$ at 25° C. were measured by using Abbe's refractometer (manufactured by Atago Co.). The refractive indexes of the inorganic fillers were measured by the solution immersion method. That is, the inorganic filler was dispersed in ethanol, 1-bromonaphthalene was added to the slurry dropwise, and the refractive index of the dispersion at a moment when the boundary between the inorganic filler and the liquid was no longer confirmed by eyes was regarded to be the refractive index of the inorganic filler. Further, the refractive index of the composite filler was calculated from the refractive indexes of the inorganic filler and of the cured product of the polymerizable monomer assuming that they can be added together.

(2) Diffusion Degree.

A curable paste was filled in a frame having a diameter of 30 mm and a thickness of 0.3 mm, photopolymerized to a sufficient degree so as to be cured, taken out from the frame, and was immersed in water maintained at 37° C. for 24 hours. The sample was measured for its distribution of luminous intensity of transmission light by using a goniophotometer (GP-2000, manufactured by Murakami Shikisai Gijyutsu Kenkyujo Co.). The diffusion degree D was calculated in accordance with the following formula, $$D=\{(I_{20}/\cos 20°)+(I_{70}/\cos 70°)\}/(2\times I_0)$$

wherein I denotes the luminous intensity of light that has passed through the sample, and $I_0$, $I_{20}$ and $I_{70}$ denote intensities of light in the directions of 0°, 20° and 70° with respect to the direction of incidence of light.

The trigonometric function represents the cosine in a direction in which the luminous intensity is measured, and the unit of angle is in degrees.

(3) Surface Smoothness.

A curable paste was filled in a square cylindrical frame having a width of 2 mm, a height of 4 mm and a length of 20 mm, photo-polymerized to a sufficient degree so as to be cured, taken out from the frame, and was immersed in water maintained at 37° C. for 24 hours. One surface of the sample was polished with a water-resistant polishing paper #1500, finish-polished for one minute by using Sof-lex Superfine (manufactured by 3M Co.), and the luster on the surface was judged by eyes. A circle ○ represents that the sample possessed an excellent smoothness, ⊙ represents that the sample possessed particularly excellent smoothness, and x represents that the sample possessed poor smoothness.

(4) Bending Strength.

A curable paste was filled in a square cylindrical frame having a size of 2×2×25 mm, photo-polymerized to a sufficient degree so as to be cured, taken out from the frame, and was immersed in water maintained at 37° C. for 24 hours. The sample was mounted on a tester (Autograph 5000D manufactured by Shimazu Seisakusho Co.) and was measured for its three-point breaking strength maintaining a distance between fulcrums of 20 mm and a cross-head speed of 0.5 mm/min.

(5) Handling Property.

Properties of the curable paste were evaluated on the following basis from the standpoint of easy filling and easy handling. That is, a mock cavity made of a plastic material was filled with the paste by using a metallic filling instrument. The paste free of the handling problems such as stickiness and crispness and which could be excellently filled, was rated as S, the paste which could be favorably handled maintaining good balance between stickiness and crispness but which adhered to the filling instrument at the time of shaping, was rated as A, the paste which was nearly free of the problem of stickiness but was powdery and easily broke was rated as B, and the paste which was very sticky, easily adhered to the filling instrument and could be handled with great difficulty was rated as C.

(6) Contraction Due to Polymerization.

An SUS plunger having a diameter of 6 mm and a height of 7 mm was inserted in an SUS split mold having a hole of a diameter of 6 mm and a height of 10 mm, and the height of the hole was set to be 3 mm. The curable paste was filled therein and with which a polypropylene film was brought into pressed contact from the upper side. The film surface facing downward was placed on a glass plate equipped with a dental visible light irradiator. A short needle capable of measuring the fine motion of a needle was brought into contact therewith from the upper side of the SUS plunger. The curable paste was cured as it was polymerized with light from the dental visible light irradiator. The contraction [%] of the cured product after 3 minutes have passed from the start of irradiation with light was calculated from the moving distance of the short needle in the up-and-down direction.

(7) Yellow Degree.

A paste of a dental curable composition was introduced into a mold having a hole measuring 7 mm in diameter and 2 mm deep. Polypropylene films were brought into pressed contact with both surfaces thereof. Both surfaces were cured by the irradiation with light each for 30 seconds by using a visible light irradiator (Power Light manufactured by Tokuyama Co.). The composition was then taken out from the mold, and was measured on the white background by using a color difference meter (TC-1800 MKII manufactured by Tokyo Denshoku Co.) to find the yellow degree (YI) in compliance with the following formula, $$\text{Yellow color degree } (YI)=100\times(1.28X-1.06Z)/Y$$

wherein X, Y and Z represent three stimulus values.

Example 1

100 Parts by weight of a polymerizable monomer M-1 in which I-1 has been dissolved as a polymerization initiator in an amount of 0.5%, was added and mixed into 300 parts by weight of the inorganic filler F-1a to prepare a paste thereof in a mortar. The paste was heated and polymerized at 95° C. in a nitrogen atmosphere for one hour. The cured product after polymerized was pulverized by using a vibration ball mill, and was treated for its surfaces by the refluxing with 0.02% by weight of the γ-methacryloyloxypropyltri- methoxysilane in ethanol at 90° C. for five hours. This was referred to as composite filler (refractive index of 1.527, average particle size of 12 μm).

To the polymerizable monomer M-1 were added a polymerization initiator CQ at a weight ratio of 0.5% and a DMPT at a weight ratio of 1.5% to prepare a homogeneous polymerizable monomer composition which was used as a matrix. Next, the organic/inorganic composite filler was introduced as a filler into an agate mortar, the above polymerizable monomer composition was gradually added thereto, and the mixture was kneaded to a sufficient degree in a dark place to prepare a homogeneous curable paste. The paste was defoamed under a reduced pressure to remove bubbles, and was, then, evaluated for its properties based on the methods described above. The composition was as shown in Table 1.

TABLE 1

| | (A) Organic/inorganic composite filler | | | | | (B) |
|---|---|---|---|---|---|---|
| | (a) Inorganic particles | (b) Polymerizable monomer | (a) Blending amount (wt %) | Average particle diameter (μm) | Refractive index $n_D^{25}$ | Inorganic fileer having average diameter not larger than 1 μm |
| Ex. 1 | F-1a | M-1 | 75 | 12 | 1.527 | — |
| Ex. 2 | F-1a | M-1 | 75 | 8 | 1.527 | — |
| Ex. 3 | F-1a | M-2 | 75 | 12 | 1.518 | — |
| Ex. 4 | F-1a | M-4 | 75 | 12 | 1.524 | — |
| Ex. 5 | F-1a | M-4 | 75 | 12 | 1.524 | — |
| Ex. 6 | F-1a | M-1 | 75 | 12 | 1.527 | — |
| Ex. 7 | F-1a | M-1 | 75 | 12 | 1.527 | F-2a |
| Ex. 8 | F-3 | M-1 | 75 | 12 | 1.519 | F-2a |
| Ex. 9 | F-1a | M-1 | 75 | 12 | 1.527 | F-2a |
| Ex. 10 | F-1a | M-1 | 75 | 12 | 1.527 | F-4 |
| Ex. 11 | F-1a | M-4 | 75 | 12 | 1.524 | F-2a |
| Ex. 12 | F-3 | M-4 | 75 | 12 | 1.516 | F-2a |
| Ex. 13 | F-1a | M-4 | 75 | 12 | 1.524 | F-2a |
| Ex. 14 | F-1a | M-4 | 75 | 12 | 1.524 | F-4 |
| Ex. 15 | F-1a | M-1 | 75 | 12 | 1.527 | F-2a |
| Ex. 16 | F-1a | M-1 | 75 | 12 | 1.527 | F-2a |
| Comp. Ex. 1 | — | — | — | — | — | F-2a |
| Comp. Ex. 2 | F-1a | M-1 | 75 | 0.8 | 1.527 | F-2a |
| Comp. Ex. 3 | F-1a | M-4 | 75 | 45 | 1.524 | F-2a |
| Comp. Ex. 4 | F-2a | M-1 | 75 | 12 | 1.545 | — |
| Comp. Ex. 5 | — | — | — | — | — | — |

| | (B') Inorganic filler having average diameter not smaller than 1 μm | | Filler weight ratio (wt %) | | | (C) Polymerizable monomer | Matrix refractive index $n_D^{25}$ | Difference of refractive index $\Delta n_D^{25}$ |
|---|---|---|---|---|---|---|---|---|
| | | Refractive index $n_D^{25}$ | A | B | B' | | | |
| Ex. 1 | — | — | 100 | 0 | 0 | M-1 | 1.546 | 0.019 |
| Ex. 2 | — | — | 100 | 0 | 0 | M-1 | 1.546 | 0.019 |
| Ex. 3 | — | — | 100 | 0 | 0 | M-1 | 1.546 | 0.028 |
| Ex. 4 | — | — | 100 | 0 | 0 | M-1 | 1.546 | 0.022 |
| Ex. 5 | — | — | 100 | 0 | 0 | M-3 | 1.550 | 0.026 |
| Ex. 6 | — | — | 100 | 0 | 0 | M-3 | 1.550 | 0.023 |
| Ex. 7 | — | — | 60 | 40 | 0 | M-1 | 1.545 | 0.018 |
| Ex. 8 | — | — | 60 | 40 | 0 | M-1 | 1.545 | 0.026 |
| Ex. 9 | — | — | 60 | 40 | 0 | M-3 | 1.547 | 0.020 |
| Ex. 10 | — | — | 60 | 40 | 0 | M-1 | 1.548 | 0.021 |
| Ex. 11 | — | — | 60 | 40 | 0 | M-1 | 1.545 | 0.021 |
| Ex. 12 | — | — | 60 | 40 | 0 | M-1 | 1.545 | 0.029 |
| Ex. 13 | — | — | 60 | 40 | 0 | M-3 | 1.547 | 0.023 |
| Ex. 14 | — | — | 60 | 40 | 0 | M-1 | 1.548 | 0.024 |
| Ex. 15 | — | — | 80 | 20 | 0 | M-1 | 1.546 | 0.019 |
| Ex. 16 | — | — | 40 | 60 | 0 | M-1 | 1.545 | 0.018 |
| Comp. Ex. 1 | — | — | 0 | 100 | 0 | M-1 | 1.545 | — |
| Comp. Ex. 2 | — | — | 60 | 40 | 0 | M-1 | 1.546 | 0.019 |
| Comp. Ex. 3 | — | — | 60 | 40 | 0 | M-1 | 1.546 | 0.022 |
| Comp. Ex. 4 | — | — | 100 | 0 | 0 | M-1 | 1.546 | 0.001 |
| Comp. Ex. 5 | F-5 | 1.530 | 0 | 0 | 100 | M-1 | 1.546 | 0.016 |

The results were as shown in Table 2.

TABLE 2

| | Filler filling rate (wt %) | Diffusion degree D | Smoothness | Bending strength (MPa) | Handling property |
|---|---|---|---|---|---|
| Ex. 1 | 76 | 0.09 | ◉ | 72 | B |
| Ex. 2 | 74 | 0.06 | ◉ | 70 | B |
| Ex. 3 | 76 | 0.16 | ◉ | 71 | B |
| Ex. 4 | 76 | 0.14 | ◉ | 71 | B |
| Ex. 5 | 76 | 0.20 | ◉ | 71 | B |
| Ex. 6 | 76 | 0.15 | ◉ | 71 | B |
| Ex. 7 | 80 | 0.13 | ◉ | 143 | A |
| Ex. 8 | 80 | 0.25 | ◉ | 141 | A |
| Ex. 9 | 80 | 0.14 | ◉ | 142 | A |
| Ex. 10 | 80 | 0.16 | ◉ | 144 | A |
| Ex. 11 | 80 | 0.19 | ◉ | 140 | A |
| Ex. 12 | 80 | 0.27 | ◉ | 142 | A |
| Ex. 13 | 80 | 0.19 | ◉ | 140 | A |
| Ex. 14 | 80 | 0.20 | ◉ | 145 | A |
| Ex. 15 | 78 | 0.11 | ◉ | 132 | A |
| Ex. 16 | 80 | 0.11 | ◉ | 136 | A |
| Comp. Ex. 1 | 65 | <0.01 | ◉ | 64 | C |

TABLE 2-continued

|  | Filler filling rate (wt %) | Diffusion degree D | Smooth-ness | Bending strength (MPa) | Handling property |
|---|---|---|---|---|---|
| Comp. Ex. 2 | 51 | <0.01 | ⊚ | 59 | C |
| Comp. Ex. 3 | 82 | 0.05 | ⊚ | 85 | C |
| Comp. Ex. 4 | 73 | <0.01 | ⊚ | 70 | B |
| Comp. Ex. 5 | 72 | 0.10 | X | 117 | B |

Examples 2 to 6

Organic composite fillers and curable pastes having compositions as shown in Table 1 were prepared by the same method as that of Example 1 to evaluate their properties.

High diffusion degrees and high surface smoothness were accomplished by using all of the compositions of Examples 1 to 6.

Example 7

By using the same polymerizable monomer composition as that of Example 1, a curable paste was prepared by replacing the filler composition by a mixture of (A) an organic/inorganic composite filler (60 parts by weight) and (B) an inorganic filler F-2a (40 parts by weight) to evaluate the properties in the same manner as in Example 1. The composition was as shown in Table 1. The results were as shown in Table 2.

Examples 8 to 16

Organic composite fillers and curable pastes having compositions as shown in Table 1 were prepared by the same method as that of Example 7 to evaluate their properties.

In Examples 7 to 16, an organic/inorganic composite filler having an average particle diameter of from 1 to 20 μm indispensable for the present invention and an inorganic filler having an average particle diameter of not larger than 1 μm were combined together. By using all of the compositions, high diffusion degrees and high surface smoothness were accomplished and, besides, further improved bending strength and paste handling property were exhibited.

Comparative Example 1

A curable paste was prepared by removing the organic/inorganic composite filler from the composition of Example 7 to evaluate the properties in the same manner as in Example 1. The composition was as shown in Table 1. The results were as shown in Table 2.

Without being blended with the organic/inorganic composite filler which is an indispensable component, the composition of Comparative Example 1 exhibited a greatly decreased diffusion degree as compared to those of Examples. Besides, the filler filling rate and the bending strength were low, and the curable paste was very sticky.

Comparative Examples 2 and 3

An organic/inorganic composite filler having a small average particle diameter (refractive index of 1.527, average particle diameter of 0.8 μm) and an organic/inorganic composite filler having a large average particle diameter (refractive index of 1.524, average particle diameter of 45 μm) were prepared by using the same composition as that of the organic/inorganic composite filler of Example 1 and by the same method as that of Example 1, but by changing the pulverizing time by using the vibration ball mill. Curable pastes were prepared by using the same matrix composition as that of Example 5 but using the above organic/inorganic composite fillers, and were evaluated for their properties in the same manner as in Example 1. The compositions were as shown in Table 1. The results were as shown in Table 2.

The organic/inorganic composite filler used in Comparative Example 2 possessed an average particle diameter smaller than the range of the present invention, and exhibited a greatly decreased diffusion degree as compared to those of Examples. Besides, the filler filling rate and the bending strength were low, and the curable paste was very sticky.

The organic/inorganic composite filler used in Comparative Example 3 possessed an average particle diameter larger than the range of the present invention, and exhibited greatly decreased bending strength. Besides, the curable paste was very powdery and sticky.

Comparative Example 4

An organic/inorganic composite filler (refractive index of 1.545, average particle diameter of 12 μm) was prepared by the same method and using the same composition as those of Example 1 but by replacing the inorganic filler F-1a which was the starting material of the organic/inorganic composite filler by F-2a. A curable paste was prepared by using the same matrix composition as that of Example 5 but using the above organic/inorganic composite filler, and was evaluated for its properties in the same manner as in Example 1. The composition was as shown in Table 1. The results were as shown in Table 2.

In Example 4, a difference in the refractive index between the organic/inorganic composite filler and the matrix after cured was smaller than 0.01. Therefore, the diffusion degree was very lower than those of Examples.

Comparative Example 5

A curable paste was prepared by using the composition of example 1 but replacing the organic/inorganic composite filler by the inorganic filler F-5, and was evaluated for its properties in the same manner as in Example 1. The composition was as shown in Table 1. The results were as shown in Table 2.

The filler used in Comparative Example 5 consisted of a single kind of inorganic particles having large diameters. Therefore, the surface smoothness was very inferior to those of Examples.

Examples 17 to 23

Curable pastes were prepared and evaluated in the same manner as in Example 11 but using the inorganic fillers F-2b to F-2h shown in Table 3 instead of (B) the inorganic filler F-2a used in Example 11. The compositions and results were as shown in Table 3.

Example 24

A curable paste was prepared by using the same inorganic filler and the same polymerizable monomer composition as those of Example 17 but by using (a) the inorganic filler F-1b for the composite filler instead of the filler F-1a, and properties were evaluated. The results were as shown in Table 3.

Examples 25 and 26

Curable pastes were prepared by using the same inorganic filler, the same organic/inorganic composite filler and the same polymerizable monomer composition as those of Example 17 but changing the filler composition into a mixture of (A) the organic/inorganic composite filler and (B) the inorganic filler F-2b at ratios of 80:20 and 40:60 (all parts by weight), and the properties were evaluated by in the same manner. The results were as shown in Table 3.

In all of the Examples 17 to 26, there were obtained curable compositions that contracted little upon polymerization before and after the curing, and of which the curable pastes could be favorably handled.

using a vibration ball mill., and were treated for their surfaces by the refluxing with 0.02% by weight of the γ-methacryloyloxypropyltrimethoxysilane in ethanol at 90° C. to obtain a composite filler having average particle size of 12 μm.

To the polymerizable monomer M-1 were added a polymerization initiator CQ at a weight ratio of 0.5% and a DMPT at a weight ratio of 1.5% to prepare homogeneous polymerizable monomer compositions. Next, 300 parts by weight of the organic/inorganic composite filler prepared by

TABLE 3

| | (A) Organic/inorganic composite filler | | | | | | Difference |
|---|---|---|---|---|---|---|---|
| | (a) Inorganic particles | (b) Polymerizable monomer | (a) Blending amount (wt %) | (B) Inorganic fileer | Filler weight ratio (wt %) A | B | of refractive index $\Delta n_D^{25}$ |
| Ex. 11 | F-1a | M-4 | 75 | F-2a | 60 | 40 | 0.021 |
| Ex. 15 | F-1a | M-4 | 75 | F-2a | 80 | 20 | 0.019 |
| Ex. 16 | F-1a | M-4 | 75 | F-2a | 40 | 60 | 0.018 |
| Ex. 17 | F-1a | M-4 | 75 | F-2b | 60 | 40 | 0.021 |
| Ex. 18 | F-1a | M-4 | 75 | F-2c | 60 | 40 | 0.021 |
| Ex. 19 | F-1a | M-4 | 75 | F-2d | 60 | 40 | 0.021 |
| Ex. 20 | F-1a | M-4 | 75 | F-2e | 60 | 40 | 0.021 |
| Ex. 21 | F-1a | M-4 | 75 | F-2f | 60 | 40 | 0.021 |
| Ex. 22 | F-1a | M-4 | 75 | F-2g | 60 | 40 | 0.021 |
| Ex. 23 | F-1a | M-4 | 75 | F-2h | 60 | 40 | 0.021 |
| Ex. 24 | F-1b | M-4 | 80 | F-2b | 60 | 40 | 0.022 |
| Ex. 25 | F-1a | M-4 | 75 | F-2b | 80 | 20 | 0.019 |
| Ex. 26 | F-1a | M-4 | 75 | F-2b | 40 | 60 | 0.018 |

| | Filler filling rate (wt %) | Contraction by polymerization (%) | Diffusion degee D | Surface smoothness | Bending strength (MPa) | Handling property |
|---|---|---|---|---|---|---|
| Ex. 11 | 80 | 1.7 | 0.19 | ◉ | 140 | A |
| Ex. 15 | 78 | 1.9 | 0.11 | ◉ | 132 | A |
| Ex. 16 | 80 | 1.7 | 0.11 | ◉ | 136 | A |
| Ex. 17 | 83 | 1.2 | 0.18 | ◉ | 141 | S |
| Ex. 18 | 83 | 1.2 | 0.17 | ◉ | 138 | S |
| Ex. 19 | 82 | 1.3 | 0.19 | ◉ | 137 | S |
| Ex. 20 | 84 | 1.1 | 0.17 | ◉ | 141 | S |
| Ex. 21 | 82 | 1.3 | 0.18 | ◉ | 136 | S |
| Ex. 22 | 83 | 1.2 | 0.20 | ◉ | 140 | S |
| Ex. 23 | 84 | 1.1 | 0.18 | ◉ | 139 | S |
| Ex. 24 | 83 | 1.2 | 0.16 | ◉ | 142 | S |
| Ex. 25 | 82 | 1.4 | 0.12 | ◉ | 130 | S |
| Ex. 26 | 83 | 1.2 | 0.14 | ◉ | 140 | S |

Examples 27 to 37

Into the polymerizable monomer M-4, there were dissolved in advance various fluorescent whitening agents shown in Table 4 at a weight ratio of 0.01% and various polymerization initiators at a weight ratio of 0.5%. 100 Parts by weight of the polymerizable monomer containing the fluorescent whitening agents and the polymerization initiators were added to 300 parts by weight of the inorganic filler F-1a in a mortar to prepare pastes thereof. The pastes were heated at 95° C. for one hour in a pressurized nitrogen atmosphere when the polymerization initiators were I-1 to I-4, and, when the polymerization initiator was I-5, were irradiated at its both surfaces with light for 30 seconds, respectively, by using a visible light irradiator (Power Light manufactured by Tokuyama Co.) so as to be cured by polymerization. The cured products were pulverized by the above-mentioned method was introduced into an agate mortar, 100 parts by weight of the above polymerizable monomer compositions were gradually added thereto, and the mixtures were kneaded to a sufficient degree in a dark place to prepare homogeneous curable pastes. The pastes were defoamed under a reduced pressure to remove bubbles, and were, then, the cured products thereof were evaluated for their properties based on the methods described above.

The compositions and results were as shown in Table 4.

In Example 27, the cured product of the polymerizable monomer composition of Example 4 corresponding to the same system except that the composite filler contained no fluorescent whitening agent, was also measured for its yellow degree (YI) to be 26.

TABLE 4

| | (A) Organic/inorganic composite filler | | (B) Inorganic fileer | Filler weight ratio (wt %) | | Fluorescent whitening agent | Difference of refractive index $\Delta n_D^{25}$ |
|---|---|---|---|---|---|---|---|
| | Fluorescent whitening agent | Polymerization initiator | | A | B | | |
| Ex. 27 | W-1 | I-1 | — | 100 | 0 | — | 0.022 |
| Ex. 28 | W-2 | I-1 | — | 100 | 0 | — | 0.022 |
| Ex. 29 | W-3 | I-1 | — | 100 | 0 | — | 0.022 |
| Ex. 30 | W-1 | I-2 | — | 100 | 0 | — | 0.022 |
| Ex. 31 | W-1 | I-3 | — | 100 | 0 | — | 0.022 |
| Ex. 32 | W-2 | I-3 | — | 100 | 0 | — | 0.022 |
| Ex. 33 | W-3 | I-3 | — | 100 | 0 | — | 0.022 |
| Ex. 34 | W-1 | I-4 | — | 100 | 0 | — | 0.022 |
| Ex. 35 | W-1 | I-5 | — | 100 | 0 | — | 0.022 |
| Ex. 36 | W-2 | I-5 | — | 100 | 0 | — | 0.022 |
| Ex. 37 | W-3 | I-5 | — | 100 | 0 | — | 0.022 |
| Ex. 38 | W-1 | I-1 | F-2a | 60 | 40 | — | 0.021 |
| Ex. 39 | W-2 | I-1 | F-2a | 60 | 40 | — | 0.021 |
| Ex. 40 | W-3 | I-2 | F-2a | 60 | 40 | — | 0.021 |
| Ex. 41 | W-1 | I-3 | F-2a | 60 | 40 | — | 0.021 |
| Ex. 42 | W-1 | I-3 | F-2a | 60 | 40 | — | 0.021 |
| Ex. 43 | W-2 | I-3 | F-2a | 60 | 40 | — | 0.021 |
| Ex. 44 | W-3 | I-3 | F-2a | 60 | 40 | — | 0.021 |
| Ex. 45 | W-1 | I-4 | F-2a | 60 | 40 | — | 0.021 |
| Ex. 46 | W-1 | I-5 | F-2a | 60 | 40 | — | 0.021 |
| Ex. 47 | W-2 | I-5 | F-2a | 60 | 40 | — | 0.021 |
| Ex. 48 | W-3 | I-5 | F-2a | 60 | 40 | — | 0.021 |
| Ex. 49 | — | I-1 | — | 100 | 0 | W-1 | 0.022 |
| Ex. 50 | — | I-1 | F-2a | 60 | 40 | W-1 | 0.021 |

| | Filler filling rate (wt %) | YI | Diffusion degee D | Surface smoothness | Bending strength (MPa) | Handling property | Contraction by polymerization (%) |
|---|---|---|---|---|---|---|---|
| Ex. 27 | 76 | 7 | 0.14 | ◎ | 73 | B | 1.7 |
| Ex. 28 | 76 | 10 | 0.12 | ◎ | 70 | B | 1.8 |
| Ex. 29 | 76 | 9 | 0.13 | ◎ | 75 | B | 1.8 |
| Ex. 30 | 76 | 7 | 0.14 | ◎ | 70 | B | 1.7 |
| Ex. 31 | 76 | 14 | 0.14 | ◎ | 68 | B | 1.9 |
| Ex. 32 | 76 | 11 | 0.13 | ◎ | 69 | B | 1.8 |
| Ex. 33 | 76 | 14 | 0.14 | ◎ | 73 | B | 1.8 |
| Ex. 34 | 76 | 14 | 0.15 | ◎ | 71 | B | 1.7 |
| Ex. 35 | 76 | 16 | 0.13 | ◎ | 68 | B | 1.8 |
| Ex. 36 | 76 | 14 | 0.14 | ◎ | 70 | B | 1.7 |
| Ex. 37 | 76 | 15 | 0.13 | ◎ | 67 | B | 1.8 |
| Ex. 38 | 80 | 6 | 0.19 | ◎ | 131 | A | 1.7 |
| Ex. 39 | 80 | 7 | 0.17 | ◎ | 136 | A | 1.7 |
| Ex. 40 | 80 | 9 | 0.18 | ◎ | 140 | A | 1.6 |
| Ex. 41 | 80 | 7 | 0.18 | ◎ | 130 | A | 1.7 |
| Ex. 42 | 80 | 10 | 0.18 | ◎ | 132 | A | 1.6 |
| Ex. 43 | 80 | 12 | 0.19 | ◎ | 133 | A | 1.6 |
| Ex. 44 | 80 | 10 | 0.18 | ◎ | 131 | A | 1.6 |
| Ex. 45 | 80 | 12 | 0.17 | ◎ | 141 | A | 1.7 |
| Ex. 46 | 80 | 12 | 0.19 | ◎ | 137 | A | 1.6 |
| Ex. 47 | 80 | 11 | 0.20 | ◎ | 132 | A | 1.6 |
| Ex. 48 | 80 | 15 | 0.18 | ◎ | 130 | A | 1.7 |
| Ex. 49 | 76 | 25 | 0.14 | ◎ | 71 | B | 1.9 |
| Ex. 50 | 80 | 21 | 0.18 | ◎ | 134 | A | 1.7 |

Examples 38 to 48

Curable pastes were prepared and evaluated in the same manner as in Example 27 but using 400 parts by weight of a mixed filler of (A) the organic/inorganic composite filler and (B) the inorganic filler F-2a mixed at ratios shown in Table 4 instead of using 300 parts by weight of the organic/inorganic composite filler used in Example 27. The compositions and results were as shown in Table 4.

In Example 38, the cured product of the polymerizable monomer composition of Example 11 corresponding to the same system except that the composite filler contained no fluorescent whitening agent, was also measured for its yellow degree (YI) to be 22.

Example 49

A curable paste was prepared and evaluated in the same manner as in Example 4 but using the polymerizable monomer composition M-1 which contained W-1 at a weight ratio of 0.01%. The composition and results were as shown in Table 4.

Example 50

A curable paste was prepared and evaluated in the same manner as in Example 11 but using the polymerizable monomer composition M-1 which contained W-1 at a weight ratio of 0.01%. The composition and results were as shown in Table 4.

In all of the compositions of Examples 27 to 48 in which the organic/inorganic composite filler was blended with the fluorescent whitening agent, there were obtained cured products having yellow degrees lower than those of when no fluorescent whitening agent was added or when the fluorescent whitening agent was simply added into the paste.

What is claimed is:

1. A dental curable composition comprising an organic/inorganic composite filler having an average particle diameter of from 1 to 20 μm and a polymerizable monomer having a (meth)acryloyl group, wherein the cured product of said dental curable composition has a diffusion degree D of not smaller than 0.01 as defined by the following formula, $$D=\{(I_{20}/\cos 20°)+(I_{70}/\cos 70°)\}/(2\times I_0)$$

wherein $I_0$, $I_{20}$ and $I_{70}$ denote intensities of light that has passed through in the directions of 0°, 20° and 70° with respect to the direction of incidence of light when light is permitted to fall perpendicularly onto the surface of a plate-like sample having a thickness of 0.3 mm obtained by curing said dental curable composition; and an inorganic filler which comprises spherical or nearly spherical inorganic particles having an average particle diameter of not larger than 1 μm and/or aggregates of said inorganic particles.

2. A dental curable composition according to claim 1, wherein the diffusion degree D is not smaller than 0.01 but is not larger than 0.5.

3. A method of producing a dental curable composition according to claim 1, wherein, in producing the dental curable composition by mixing a polymerizable monomer having a (meth)acryloyl group composition and an organic/inorganic composite filler having an average particle diameter of from 1 to 20 μm together, a refractive index of said organic/inorganic composite filler and a refractive index of the cured product obtained by curing said polymerizable monomer composition, are so adjusted that a difference therebetween is not smaller than, 0.01 in an absolute value.

4. A method of producing a dental curable composition according to claim 3, wherein a refractive index of said organic/inorganic composite filler and a refractive index of the cured product obtained by curing said polymerizable monomer composition, are so adjusted that a difference therebetween is not smaller than 0.01 but is not larger than 0.04 in an absolute value.

5. The dental curable composition according to claim 1, wherein the organic/inorganic composite filler is obtained by pulverizing a cured product of a polymerizable and curable composition containing a polymerizable monomer and spherical or nearly spherical inorganic particles having an average particle diameter of from 0.001 to 1 μm and/or aggregates of said inorganic particles.

6. A dental curable composition according to claim 5, wherein the inorganic particles and/or the aggregates of the inorganic particles comprising the organic/inorganic composite filler, are chiefly constituted by an inorganic oxide obtained by reacting an organosilicon compound which is hydrolyzable and an organic compound of at least one metal selected from the group consisting of metals of the Groups I, II, III and IV of periodic table which can be bonded to the organosilicon compound which is hydrolyzable.

7. The dental curable composition according to claim 5, wherein the inorganic filler is surface treated for its surfaces with a silane compound represented by the following general formula, $$CH_2=C(R^1)-COO-(CH_2)_n-Si-R^2{}_mR^3{}_{(3-m)} \qquad (I)$$

wherein $R^1$ is a hydrogen atom or a methyl group, $R^2$ is an alkoxy group having 1 to 6 carbon atoms, an isocyanate group or a chlorine atom, $R^3$ is a hydrocarbon group having 1 to 6 carbon atoms, m is 2 or 3, and n is an integer of 8 to 20.

8. The dental curable composition according to claim 1, wherein the organic/inorganic composite filler contains a fluorescent whitening agent.

9. The dental curable composition according to claim 8, wherein the cured product has a yellowness index (YI) of not larger than 20 as defined by the following formula, Yellowness index $(YI)=100\times(1.28X-1.06Z)/Y$ wherein X, Y and Z are three stimulus values of when a sample having a thickness of 2 mm is measured using a color-difference meter with the sample being closely adhered to a white background.

10. The dental curable composition according to claim 1, wherein the polymerizable monomer comprising the dental curable composition forms a cured product thereof having a refractive index which is different in an absolute value from the refractive index of the cured product of the polymerizable composition used as the starting material of the organic/inorganic composite filler by from 0.005 to 0.05.

11. A dental curable composition comprising an organic/inorganic composite filler and a polymerizable monomer having a (meth)acryloyl group, the organic/inorganic composite filler satisfying the following conditions (1) and (2):

(1) an average particle diameter is from 1 to 20 μm; and (2) when a refractive index thereof is denoted by $n_F$ and a refractive index of a matrix portion in which said organic/inorganic composite filler is dispersed in a cured product obtained by curing said dental curable composition, is denoted by $n_M$, then an absolute value of $n_F-n_M$ is not smaller than 0.01; and further comprising an inorganic filler which comprises spherical or nearly spherical inorganic particles having an average particle diameter of not larger than 1 μm and/or aggregates of said inorganic particles.

12. A dental curable composition comprising an organic/inorganic composite filler and a polymerizable monomer having a (meth)acryloyl group, the organic/inorganic composite filler satisfying the following conditions (1) and (2):

(1) an average particle diameter is from 1 to 20 μm; and (2) when a refractive index thereof is denoted by $n_F$ and a refractive index of a matrix portion in which said organic/inorganic composite filler is dispersed in a cured product obtained by curing said dental curable composition, is denoted by $n_M$, then an absolute value of $n_F-n_M$ is not smaller than 0.01;

further comprising an inorganic filler which comprises spherical or nearly spherical inorganic particles having an average particle diameter of not larger than 1 μm and/or aggregates of said inorganic particles; and wherein the inorganic filler is surface treated with a silane compound represented by the following general formula, $$CH_2=C(R^1)-COO-(CH_2)_n-Si-R^2{}_mR^3{}_{(3-m)} \qquad (I)$$

wherein $R^1$ is a hydrogen atom or a methyl group, $R^2$ is an alkoxy group having 1 to 6 carbon atoms, an isocyanate group or a chlorine atom, $R^3$ is a hydrocarbon group having 1 to 6 carbon atoms, m is 2 or 3, and n is an integer of 8 to 20.

13. A dental curable composition comprising an organic/inorganic composite filler and a polymerizable monomer having a (meth)acryloyl group, the organic/inorganic composite filler satisfying the following conditions (1) and (2):

(1) an average particle diameter is from 1 to 20 μm; and (2) when a refractive index thereof is denoted by $n_F$ and a refractive index of a matrix portion in which said organic/inorganic composite filler is dispersed in a cured product obtained by curing said dental curable composition, is denoted by $n_M$, then an absolute value of $n_F-n_M$ is not smaller than 0.01; and wherein the organic/inorganic composite filler contains a fluorescent whitening agent.

14. A dental curable composition comprising an organic/inorganic composite filler and a polymerizable monomer having a (meth)acryloyl group, the organic/inorganic composite filler satisfying the following conditions (1) and (2):

(1) an average particle diameter is from 1 to 20 μm; and (2) when a refractive index thereof is denoted by $n_F$ and a refractive index of a matrix portion in which said organic/inorganic composite filler is dispersed in a cured product obtained by curing said dental curable composition, is denoted by $n_M$, then an absolute value of $n_F-n_M$ is not smaller than 0.01;

wherein the organic/inorganic composite filler contains a fluorescent whitening agent; and wherein the cured product has a yellowness index (YI) of not larger than 20 as defined by the following formula, $$\text{Yellowness index } (YI) = 100 \times (1.28X - 1.06Z)/Y$$

wherein X, Y and Z are three stimulus values of when a sample having a thickness of 2 mm is measured using a color-difference meter with the sample being closely adhered to a white background.

* * * * *